(12) United States Patent
Salahieh et al.

(10) Patent No.: US 8,267,956 B2
(45) Date of Patent: Sep. 18, 2012

(54) VASCULAR EMBOLIC FILTER EXCHANGE DEVICES AND METHODS OF USE THEREOF

(75) Inventors: Amr Salahieh, Saratoga, CA (US); Jackson Demond, Santa Cruz, CA (US); Jeff Krolik, Campbell, CA (US)

(73) Assignee: Incept, LLC, San Mateo, CA (US)

( * ) Notice: Subject to any disclaimer, the term of this patent is extended or adjusted under 35 U.S.C. 154(b) by 0 days.

(21) Appl. No.: 13/170,378

(22) Filed: Jun. 28, 2011

(65) Prior Publication Data

US 2011/0257678 A1    Oct. 20, 2011

Related U.S. Application Data

(63) Continuation of application No. 11/092,249, filed on Mar. 29, 2005, now Pat. No. 7,981,134, which is a continuation of application No. 10/045,628, filed on Oct. 19, 2001, now Pat. No. 6,887,257.

(51) Int. Cl.
*A61M 29/00* (2006.01)

(52) U.S. Cl. .................... 606/200; 604/96.01

(58) Field of Classification Search .......... 606/108, 606/159, 194, 200; 604/96.01
See application file for complete search history.

(56) References Cited

U.S. PATENT DOCUMENTS

| | | | |
|---|---|---|---|
| 3,472,230 A | 10/1969 | Fogarty | |
| 3,952,747 A | 4/1976 | Kimmell, Jr. | |
| 3,996,938 A | 12/1976 | Clark, III | |
| 4,046,150 A | 9/1977 | Schwartz et al. | |
| 4,425,908 A | 1/1984 | Simon | |
| 4,590,938 A | 5/1986 | Segura et al. | |
| 4,619,246 A | 10/1986 | Molgaard-Nielsen et al. | |
| 4,643,184 A | 2/1987 | Mobin-Uddin | |
| 4,650,466 A | 3/1987 | Luther | |
| 4,662,885 A | 5/1987 | DiPisa, Jr. | |
| 4,706,671 A | 11/1987 | Weinrib | |
| 4,723,549 A | 2/1988 | Wholey et al. | |
| 4,790,812 A | 12/1988 | Hawkins, Jr. et al. | |
| 4,790,813 A | 12/1988 | Kensey | |
| 4,794,928 A | 1/1989 | Kletschka | |
| 4,807,626 A | 2/1989 | McGirr | |
| 4,842,579 A | 6/1989 | Shiber | |
| 4,857,045 A | 8/1989 | Rydell | |

(Continued)

FOREIGN PATENT DOCUMENTS

DE    2821048 B1    7/1980

(Continued)

OTHER PUBLICATIONS

"Aerosclerotic Disease of the Aortic Arch as a Risk Factor of Recurrent Ischemic Stroke," The New England Journal of Medicine, pp. 1216-1221 (May 1996).

(Continued)

*Primary Examiner* — Victor Nguyen
(74) *Attorney, Agent, or Firm* — Seager, Tufte & Wickhem LLC

(57) ABSTRACT

Vascular embolic filtering systems, as well as methods for using the same, are provided. In general, the subject invention includes a system comprised of a delivery and retrieval sheath adapted for delivering and retrieving multiple embolic filters, wherein the embolic filters are each operatively coupled to a distal region of a filter wire segment and are deployable within a target vessel.

11 Claims, 7 Drawing Sheets

U.S. PATENT DOCUMENTS

| | | | |
|---|---|---|---|
| 4,873,978 A | 10/1989 | Ginsburg | |
| 4,886,061 A | 12/1989 | Fischell et al. | |
| 4,921,478 A | 5/1990 | Solano et al. | |
| 4,921,484 A | 5/1990 | Hillstead | |
| 4,926,858 A | 5/1990 | Gifford, III et al. | |
| 4,969,891 A | 11/1990 | Gewertz | |
| 4,998,539 A | 3/1991 | Delsanti | |
| 5,002,560 A | 3/1991 | Machold et al. | |
| 5,011,488 A | 4/1991 | Ginsburg | |
| 5,053,008 A | 10/1991 | Bajaj | |
| 5,071,407 A | 12/1991 | Termin et al. | |
| 5,100,423 A | 3/1992 | Fearnot | |
| 5,102,415 A | 4/1992 | Guenther et al. | |
| 5,133,733 A | 7/1992 | Rasmussen et al. | |
| 5,152,771 A | 10/1992 | Sabbaghian et al. | |
| 5,152,777 A | 10/1992 | Goldberg et al. | |
| 5,160,342 A | 11/1992 | Reger et al. | |
| 5,192,286 A | 3/1993 | Phan et al. | |
| 5,197,976 A * | 3/1993 | Herweck et al. | 623/1.27 |
| 5,224,953 A | 7/1993 | Morgentaler | |
| 5,324,304 A | 6/1994 | Rasmussen | |
| 5,329,942 A | 7/1994 | Gunther et al. | |
| 5,330,484 A | 7/1994 | Gunther | |
| 5,354,310 A | 10/1994 | Garnie et al. | |
| 5,370,657 A | 12/1994 | Irie | |
| 5,376,100 A | 12/1994 | Lefebvre | |
| 5,415,630 A | 5/1995 | Gory et al. | |
| 5,419,774 A | 5/1995 | Willard et al. | |
| 5,421,832 A | 6/1995 | Lefebvre | |
| 5,423,742 A | 6/1995 | Theron | |
| 5,449,372 A | 9/1995 | Schmaltz et al. | |
| 5,456,667 A | 10/1995 | Ham et al. | |
| 5,462,529 A | 10/1995 | Simpson et al. | |
| 5,536,242 A | 7/1996 | Willard et al. | |
| 5,549,626 A | 8/1996 | Miller et al. | |
| 5,658,296 A | 8/1997 | Bates et al. | |
| 5,662,671 A | 9/1997 | Barbut et al. | |
| 5,669,933 A | 9/1997 | Simon et al. | |
| 5,695,519 A | 12/1997 | Summers et al. | |
| 5,713,917 A | 2/1998 | Leonhardt et al. | |
| 5,720,764 A | 2/1998 | Naderlinger | |
| 5,728,066 A | 3/1998 | Daneshvar | |
| 5,749,848 A | 5/1998 | Jang et al. | |
| 5,769,816 A | 6/1998 | Barbut et al. | |
| 5,779,716 A | 7/1998 | Cano et al. | |
| 5,792,157 A | 8/1998 | Mische et al. | |
| 5,795,322 A | 8/1998 | Boudewijn | |
| 5,800,457 A | 9/1998 | Gelbfish | |
| 5,800,525 A | 9/1998 | Bachinski et al. | |
| 5,807,398 A | 9/1998 | Shaknovich | |
| 5,810,874 A | 9/1998 | Lefebvre | |
| 5,814,064 A | 9/1998 | Daniel et al. | |
| 5,827,324 A | 10/1998 | Cassell et al. | |
| 5,833,644 A | 11/1998 | Zadno-Azizi et al. | |
| 5,833,650 A | 11/1998 | Imran | |
| 5,846,260 A | 12/1998 | Maahs | |
| 5,848,964 A | 12/1998 | Samuels | |
| 5,876,367 A | 3/1999 | Kaganov et al. | |
| 5,895,399 A | 4/1999 | Barbut et al. | |
| 5,910,154 A | 6/1999 | Tsugita et al. | |
| 5,911,734 A | 6/1999 | Tsugita et al. | |
| 5,925,016 A | 7/1999 | Chornenky et al. | |
| 5,925,060 A | 7/1999 | Forber | |
| 5,925,062 A | 7/1999 | Purdy | |
| 5,935,139 A | 8/1999 | Bates | |
| 5,941,869 A | 8/1999 | Patterson et al. | |
| 5,941,896 A | 8/1999 | Kerr | |
| 5,947,995 A | 9/1999 | Samuels | |
| 5,954,745 A | 9/1999 | Gertler et al. | |
| 5,980,555 A | 11/1999 | Barbut et al. | |
| 5,989,281 A | 11/1999 | Barbut et al. | |
| 5,993,469 A | 11/1999 | McKenzie et al. | |
| 5,997,557 A | 12/1999 | Barbut et al. | |
| 6,001,118 A | 12/1999 | Daniel et al. | |
| 6,007,557 A | 12/1999 | Ambrisco et al. | |
| 6,010,522 A | 1/2000 | Barbut et al. | |
| 6,013,085 A | 1/2000 | Howard | |
| 6,027,520 A | 2/2000 | Tsugita et al. | |
| 6,042,598 A | 3/2000 | Tsugita et al. | |
| 6,051,014 A | 4/2000 | Jang | |
| 6,051,015 A | 4/2000 | Maahs | |
| 6,053,932 A | 4/2000 | Daniel et al. | |
| 6,059,814 A | 5/2000 | Ladd | |
| 6,066,149 A | 5/2000 | Samson et al. | |
| 6,066,158 A | 5/2000 | Engelson et al. | |
| 6,068,645 A | 5/2000 | Tu | |
| 6,086,605 A | 7/2000 | Barbut et al. | |
| 6,117,154 A | 9/2000 | Barbut et al. | |
| 6,129,739 A | 10/2000 | Khosravi | |
| 6,136,016 A | 10/2000 | Barbut et al. | |
| 6,142,987 A | 11/2000 | Tsugita | |
| 6,152,946 A | 11/2000 | Broome et al. | |
| 6,165,200 A | 12/2000 | Tsugita et al. | |
| 6,168,579 B1 | 1/2001 | Tsugita et al. | |
| 6,171,327 B1 * | 1/2001 | Daniel et al. | 606/200 |
| 6,171,328 B1 | 1/2001 | Addis | |
| 6,179,851 B1 | 1/2001 | Barbut et al. | |
| 6,179,859 B1 | 1/2001 | Bates et al. | |
| 6,179,861 B1 | 1/2001 | Khosravi et al. | |
| 6,203,561 B1 | 3/2001 | Ramee et al. | |
| 6,206,868 B1 | 3/2001 | Parodi | |
| 6,214,026 B1 | 4/2001 | Lepak et al. | |
| 6,221,006 B1 | 4/2001 | Dubrul et al. | |
| 6,224,620 B1 | 5/2001 | Maahs | |
| 6,231,544 B1 | 5/2001 | Tsugita et al. | |
| 6,235,044 B1 | 5/2001 | Root et al. | |
| 6,235,045 B1 | 5/2001 | Barbut et al. | |
| 6,238,412 B1 | 5/2001 | Dubrul et al. | |
| 6,245,087 B1 | 6/2001 | Addis | |
| 6,245,088 B1 | 6/2001 | Lowery | |
| 6,245,089 B1 | 6/2001 | Daniel et al. | |
| 6,258,115 B1 | 7/2001 | Dubrul | |
| 6,264,663 B1 | 7/2001 | Cano | |
| 6,264,672 B1 | 7/2001 | Fisher | |
| 6,270,513 B1 | 8/2001 | Tsugita et al. | |
| 6,277,138 B1 | 8/2001 | Levinson et al. | |
| 6,277,139 B1 | 8/2001 | Levinson et al. | |
| 6,280,413 B1 | 8/2001 | Clark et al. | |
| 6,287,321 B1 | 9/2001 | Jang | |
| 6,290,710 B1 | 9/2001 | Cryer et al. | |
| 6,309,399 B1 | 10/2001 | Barbut et al. | |
| 6,319,268 B1 | 11/2001 | Ambrisco et al. | |
| 6,344,049 B1 | 2/2002 | Levinson et al. | |
| 6,602,271 B2 | 8/2003 | Adams et al. | |
| 6,605,102 B1 | 8/2003 | Mazzocchi et al. | |
| 6,616,682 B2 | 9/2003 | Joergensen et al. | |
| 2002/0095141 A1 | 7/2002 | Belef et al. | |
| 2002/0095171 A1 | 7/2002 | Belef et al. | |

FOREIGN PATENT DOCUMENTS

| | | |
|---|---|---|
| DE | 3417738 A1 | 11/1985 |
| DE | 4030998 A1 | 10/1990 |
| DE | 19916162 A1 | 10/2000 |
| EP | 0200688 A1 | 11/1986 |
| EP | 0293605 A1 | 12/1988 |
| EP | 0411118 A1 | 2/1991 |
| EP | 0427429 A2 | 5/1991 |
| EP | 0437121 B2 | 7/1991 |
| EP | 0472334 A1 | 2/1992 |
| EP | 0472368 A2 | 2/1992 |
| EP | 0533511 A1 | 3/1993 |
| EP | 0655228 A1 | 11/1994 |
| EP | 0686379 A2 | 6/1995 |
| EP | 0696447 A2 | 2/1996 |
| EP | 0737450 A1 | 10/1996 |
| EP | 0743046 A1 | 11/1996 |
| EP | 0759287 A1 | 2/1997 |
| EP | 0771549 A2 | 5/1997 |
| EP | 0784988 A1 | 7/1997 |
| EP | 0852132 A1 | 7/1998 |
| EP | 0934729 A1 | 8/1999 |
| FR | 2580504 A1 | 10/1986 |
| FR | 2643250 A1 | 8/1990 |
| FR | 2666980 A1 | 3/1992 |
| FR | 2694687 A1 | 8/1992 |
| FR | 2768326 A1 | 3/1999 |
| GB | 2020557 B | 1/1983 |

| | | | |
|---|---|---|---|
| JP | 8187294 | A | 7/1996 |
| SU | 764684 | A1 | 9/1980 |
| WO | 8809683 | A1 | 12/1988 |
| WO | 9203097 | A1 | 3/1992 |
| WO | 9414389 | A1 | 7/1994 |
| WO | 9424946 | A1 | 11/1994 |
| WO | 9601591 | A1 | 1/1996 |
| WO | 9604875 | A1 | 2/1996 |
| WO | 9610375 | A1 | 4/1996 |
| WO | 9619941 | A1 | 7/1996 |
| WO | 9623441 | A1 | 8/1996 |
| WO | 9633677 | A1 | 10/1996 |
| WO | 9717100 | A1 | 5/1997 |
| WO | 9727808 | A1 | 8/1997 |
| WO | 9742879 | A1 | 11/1997 |
| WO | 9802084 | A2 | 1/1998 |
| WO | 9802112 | A1 | 1/1998 |
| WO | 9823322 | A1 | 6/1998 |
| WO | 9833443 | A1 | 8/1998 |
| WO | 9834673 | A1 | 8/1998 |
| WO | 9836786 | A1 | 8/1998 |
| WO | 9838920 | A1 | 9/1998 |
| WO | 9838929 | A1 | 9/1998 |
| WO | 9839046 | A1 | 9/1998 |
| WO | 9839053 | A1 | 9/1998 |
| WO | 9846297 | A1 | 10/1998 |
| WO | 9847447 | A1 | 10/1998 |
| WO | 9849952 | A1 | 11/1998 |
| WO | 9850103 | A1 | 11/1998 |
| WO | 9851237 | A1 | 11/1998 |
| WO | 9855175 | A1 | 12/1998 |
| WO | 9909895 | A1 | 3/1999 |
| WO | 9922673 | A1 | 5/1999 |
| WO | 9923976 | A1 | 5/1999 |
| WO | 9925252 | A1 | 5/1999 |
| WO | 9930766 | A1 | 6/1999 |
| WO | 9940964 | A1 | 8/1999 |
| WO | 9942059 | A2 | 8/1999 |
| WO | 9944510 | A1 | 9/1999 |
| WO | 9944542 | A2 | 9/1999 |
| WO | 9955236 | A1 | 11/1999 |
| WO | 9958068 | A2 | 11/1999 |
| WO | 0007521 | A1 | 2/2000 |
| WO | 0007655 | A1 | 2/2000 |
| WO | 0009054 | A1 | 2/2000 |
| WO | 0016705 | A1 | 3/2000 |
| WO | 0049970 | A1 | 8/2000 |
| WO | 0053120 | A1 | 9/2000 |
| WO | 0067664 | A1 | 11/2000 |
| WO | 0067665 | A1 | 11/2000 |
| WO | 0067666 | A1 | 11/2000 |
| WO | 0067668 | A1 | 11/2000 |
| WO | 0067669 | A1 | 11/2000 |
| WO | 0076390 | A1 | 12/2000 |
| WO | 0105462 | A1 | 1/2001 |
| WO | 0108595 | A1 | 2/2001 |
| WO | 0108596 | A1 | 2/2001 |
| WO | 0108742 | A1 | 2/2001 |
| WO | 0108743 | A1 | 2/2001 |
| WO | 0110320 | A1 | 2/2001 |
| WO | 0115629 | A1 | 3/2001 |
| WO | 0121077 | A1 | 3/2001 |
| WO | 0121100 | A1 | 3/2001 |
| WO | 0126726 | A1 | 4/2001 |
| WO | 0135857 | A1 | 5/2001 |
| WO | 0143662 | A1 | 6/2001 |
| WO | 0147579 | A1 | 7/2001 |
| WO | 0149208 | A1 | 7/2001 |
| WO | 0149209 | A1 | 7/2001 |
| WO | 0149215 | A2 | 7/2001 |
| WO | 0149355 | A1 | 7/2001 |
| WO | 0152768 | A1 | 7/2001 |
| WO | 0158382 | A2 | 8/2001 |
| WO | 0160442 | A1 | 8/2001 |
| WO | 0167989 | A2 | 9/2001 |
| WO | 0170326 | A1 | 9/2001 |
| WO | 0172205 | A2 | 10/2001 |
| WO | 0187183 | A2 | 11/2001 |
| WO | 0189413 | A2 | 11/2001 |
| WO | 0191824 | A2 | 12/2001 |
| WO | 02054988 | A2 | 7/2002 |

OTHER PUBLICATIONS

"Endovascular Grafts, Stents Drive Interventional Radiology Growth," Cardiovascular Device Update, 2(3):1-12 (Mar. 1996).
"Protruding Atheromas in the Thoracic Aortic and Systemic Embolization," pp. 423-427 American College of Physicians (1991).
"Recognition and Embolic Potential of Intraaortic Atherosclerotic Debris," American College of Cardiology (Jan. 1991).
Cragg, Andrew et al., "A New Percutaneous Vena Cava Filger," AJR, 141:601-604 (Sep. 1983).
Cragg, Andrew et al., "Nonsurgical Placement of Arterial Endoprosthesis: A New Technique Using Nitinol Wire," AJR, pp. 261-263 (Apr. 1983).
Diethrich et al., "Percutaneous Techniques for Endoluminal Carotid Interventions," J. Endovasc. Surg., 3:182-202 (1996).
Fadali, A. Moneim, "A filtering device for the prevention of particulate embolization during the course of cardiac surgery," Surgery, 64(3) 634-639 (Sep. 1968).
Haissaguerre et al., "Spontaneous Initiation of Atrial Fibrillation by Ectopic Beats Originating in the Pulmonary Veins," The New England Journal of Medicine, 339(10):650-666 (Sep. 1988).
Jordan, Jr. et al., "Microemboli Detected by Transcranial Doppler Monitoring . . . ," Cardiovascular Surgery, 7(1)33-38 (Jan. 1999).
Lesch, "Can Catheter Ablation Cure Atrial Fibrillation?" ACC Current Journal Review, pp. 38-40, (Sep./Oct. 1997).
Lund et al., "Long-Term Patentcy of Ductus After Balloon Dilation: an Experimental Study," Laboratory Investigation, 69(4):772-774 (Apr. 1984).
Marache et al., "Percutaneous Transluminal Venous Angioplasty . . . ," American Heart Journal, 125(2 Pt 1):362-366 (Feb. 1993).
Mazur et al., "Directional Atherectomy with the Omnicath.TM: A Unique New Catheter System," Catheterization and Cardiovascular Diagnosis, 31:17-84 (1994).
Moussa, MD, Issaam "Stents Don't Require Systemic Anticoagulation . . . But the Technique (and Results) Must be Optimal," Journal of Invasive Cardiol., 8(E):3E-7E, (1996).
Nakanishi et al., "Catheter Intervention to Venous System Using Expandable Metallic Stents," Rinsho Kyobu Geka, 14 (2):English Abstract Only (Apr. 1994).
Onal et al., "Primary Stenting for Complex Atherosclerotic Plaques in Aortic and Iliac Stenoses." Cardiovascular & Interventional Radiology, 21(5):386-392 (1998).
Theron et al., "New Triple Coaxial Catheter System for Carotid Angioplasty with Cerebral Protection," American Journal of Neuroradiology, 11:869-874 (1990).
Tunick et al., "Protruding atherosclerotic plaque in the aortic arch of patients with systemic embolization: A new finding seen by transesophageal echocardiography," American Heart Journal 120(3):658-660 (Sep. 1990).
Waksman et al., "Distal Embolization is Common After Directional Atherectomy . . . ," American Heart Journal, 129 (3):430-435 (1995).
Wholey, Mark H. et al., PTA and Stents in the Treatment of Extracranial Circulation, The Journal of Invasive Cardiology, 8(E)25E-30E (1996).

* cited by examiner

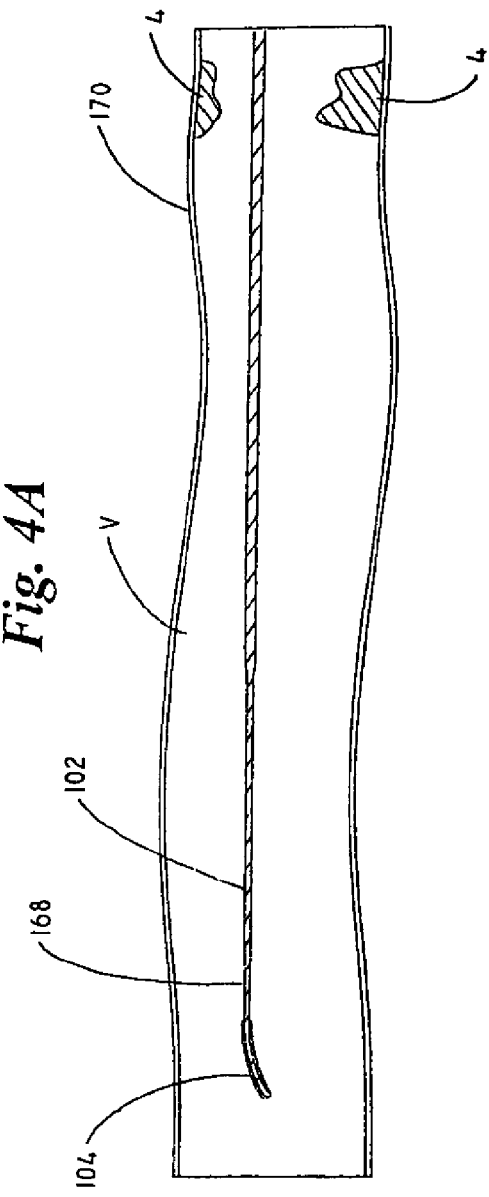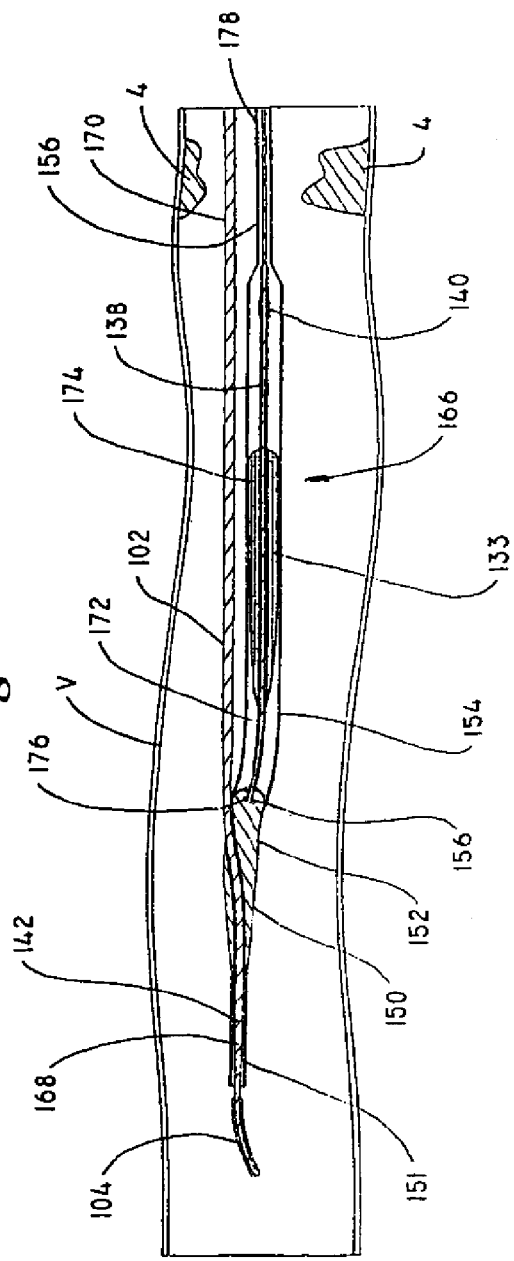

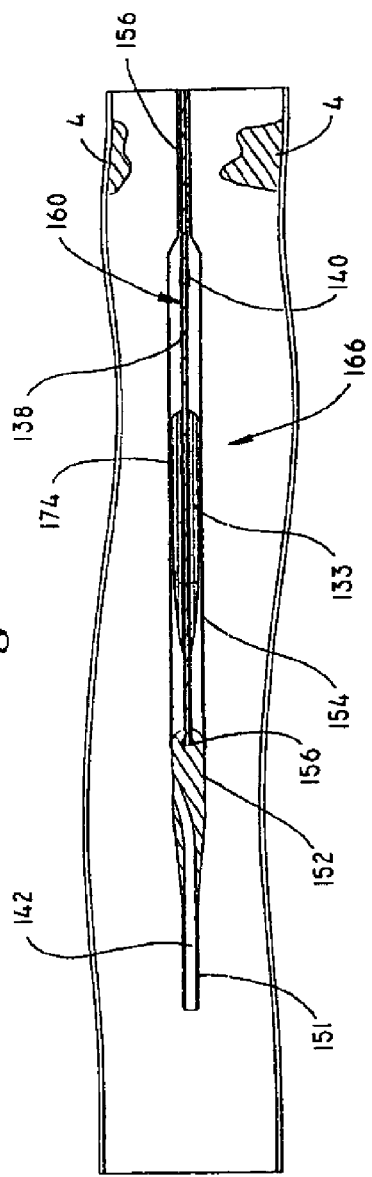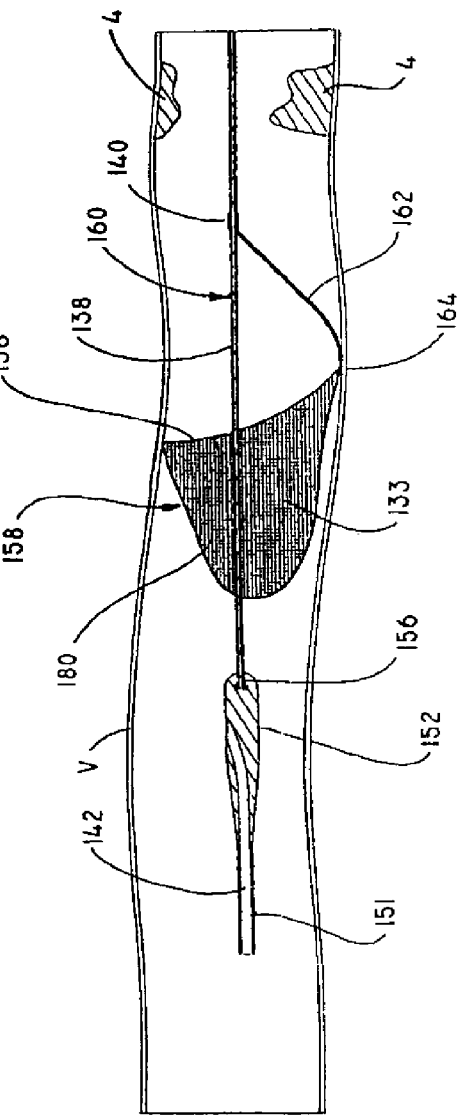

VASCULAR EMBOLIC FILTER EXCHANGE DEVICES AND METHODS OF USE THEREOF

RELATED APPLICATIONS

This application is a continuation of U.S. application Ser. No. 11/092,249 filed Mar. 29, 2005, which is a continuation of U.S. application Ser. No. 10/045,628 filed Oct. 19, 2001, now U.S. Pat. No. 6,887,257.

FIELD OF THE INVENTION

The present invention relates to systems and methods for filtering and removing matter from within the vasculature. More particularly, the invention is directed to the intravascular exchange of intravascular devices useful for capturing emboli generated during interventional procedures, and for thrombectomy and embolectomy procedures.

BACKGROUND OF THE INVENTION

Vascular procedures to treat occlusive vascular diseases, such as angioplasty, atherectomy and stent placement, often cause blood clots to form and/or material to dislodge from inside the vessel walls and enter the bloodstream. The dislodged material (e.g., plaque), known as emboli, may be large enough to occlude smaller downstream vessels, potentially blocking blood flow to tissue. Additionally, the blood clots, known as thrombi, may be large enough or grow over time to form a blockage at the interventional site or at another downstream location should the thrombus become released into the bloodstream.

There are numerous previously known interventional systems and methods that employ a filter mechanism designed to capture material liberated from vessel walls during the treatment or diagnosis of vascular disease. Many of the more recent devices employ radially expandable filters disposed at the distal end of a guide wire. These filters have various configurations, such as mesh or microporous membranes in the form of sleeves, parachutes or baskets attached to the guide wire or other delivery mechanism by means of struts, wires, ribs or frames. The meshes are frequently made of woven or braided fibers or wires made of stainless steel, nitinol, platinum alloy, polyester, nylon or porous plastics, for example. The microporous membranes are typically made of a polymer material such as polypropylene, polyurethane, polyester, polyethylene tetraphlalate, polytetrafluoroethylene or combinations thereof.

Examples of procedures employing such filters include angioplasty, atherectomy, thrombectomy and stent placement. These procedures typically involve transluminally inserting and delivering within a vessel, a guide wire with an attached filter to a location distal to a lesion or treatment site, and deploying the filter. The interventional device is then delivered over the guide wire to the treatment site. During the treatment of a lesion within the patient's vessel, plaque is often liberated from the walls of the vessel creating emboli within the bloodstream. These emboli are then captured within the deployed filter, where they remain for the duration of the treatment procedure.

Depending on the amount of plaque dislodged from the vessel wall, the embolic filter may become occluded with emboli during an interventional procedure, thus preventing blood from flowing through the filter. As a result, a pool forms proximal to the filter. When the filter becomes full or occluded with emboli and debris, the interventional procedure may need to be terminated so that the filter can be removed from the vasculature. As such, the duration of the interventional procedure is dependent upon the emboli-filling capacity of the deployed filter.

Numerous approaches have been postulated to overcome the increased procedure times associated with the retrieval and subsequent exchange of emboli-laden filters from a patient's vasculature. For example, one such approach is to employ an aspiration device to aspirate emboli contained within a filter sac of a vascular filter, so as to eliminate the need to retrieve and exchange the filter when it becomes full of emboli. However, there are significant disadvantages associated with this approach, including increased procedural complexity, the need for additional components and the inability to completely aspirate emboli entrapped in the filter pores.

In view of the description of the foregoing devices and methods, it is desirable to provide an improved embolic filter system. Additionally, it is desirable to have such systems that provide for the rapid exchange of embolic filters during the course of an interventional diagnostic or therapeutic procedure and/or in which a stent is deployed. Further, it is advantageous to have such systems capable of delivering multiple filters and/or interventional devices without losing guide wire access to the target site. In addition, it is desirable that there be a safe withdrawal of the deployed embolic filters from the vasculature. It is also desirable to first insert a guide wire distal the target region, and then subsequently replace the guide wire with a filter wire attached to a filter. Insertion of a guide wire first, and then subsequently replacing the guide wire with a filter and filter wire, enables the clinician to more accurately maneuver the embolic filter across the site of the lesion.

SUMMARY OF THE INVENTION

The present invention pertains to embolic protection systems deployed in a body vessel or cavity for the collection of loosened and/or dislodged debris, such as embolic material dislodged during, or thrombi formed as a result of, an interventional procedure. The present invention is particularly helpful to protect the vasculature of a patient from dislodged emboli during interventional procedures such as angioplasty, atherectomy, thrombectomy, embolectomy, intravascular diagnostic and stent placement procedures by enabling rapid exchange of embolic filters during the course of the interventional procedure.

Vascular embolic filter systems, as well as methods for using the same, are provided. In one particular embodiment, the subject invention includes a system comprised of an embolic filter assembly and a multiple lumen delivery and retrieval sheath, where the embolic filter assembly includes a guide wire with an embolic filter operatively coupled to the guide wire for capturing emboli created during interventional procedures within a target vessel. Features of the subject systems provide for the rapid exchange and deployment of embolic filters in a patient's vasculature. Rapid exchange of embolic filters during the course of a procedure decreases overall procedure times and minimizes the risks associated with occluded embolic filters.

Specifically, the rapid exchange of embolic filters is accomplished by sequentially retrieving an occluded filter and deploying a second, unused or unoccluded filter through a single delivery and retrieval sheath having at least two lumens, without having to remove the occluded filter and/or the sheath prior to delivering and deploying the second filter.

As such, a first embolic filter is deployed to a target site distal to a stenosis such that the first deployed embolic filter creates an opening or mouth through which emboli and debris can flow. Once a first embolic filter is deployed, an interventional device can be advanced to the site of the stenosis and the interventional procedure may commence. Once filled with emboli and debris, the interventional device is removed from the vessel. The multiple lumen delivery and retrieval sheath of the present invention is then advanced over the guide wire in order to retrieve the first embolic filter and to deliver and deploy a second embolic filter. The guide wire with the first embolic filter attached is pulled or retracted into the first lumen of the sheath, or alternatively the sheath is advanced over the guide wire and attached embolic filter, causing the filter opening or mouth to close or collapse. Such withdrawal prevents emboli collected during the procedure from escaping into the patient's blood. Once the first embolic filter is effectively withdrawn into a lumen of the delivery and retrieval sheath so as to prevent the escape of collected emboli, a second embolic filter can be deployed to the target site through a second lumen of the delivery and retrieval sheath. Again, when filled with emboli and debris, the second deployed embolic filter can also be retrieved by withdrawing it at least partially into a second lumen of the delivery and retrieval sheath in order to sufficiently close or collapse the filter mouth to prevent the escape of emboli from the embolic filter. Additional filters can also be rapidly advanced, deployed and retrieved as described above, in certain embodiments through additional lumens within the multiple lumen delivery and retrieval sheath.

In another embodiment of the present invention, an interventional device such as an angioplasty catheter, embolectomy device, atherectomy device or the like is advanced to the procedure site through one of the lumens of the multiple lumen delivery and retrieval sheath of the present invention. In certain embodiments, embolic filter exchange and the interventional procedure can occur without the need to remove the sheath from the vasculature between exchanges, thus further reducing procedure times.

In yet another embodiment of the present invention, a guide wire shaft defining a guide wire lumen is operatively coupled to a filter wire. The guide wire shaft, along with the filter wire, can be advanced along a guide wire to point distal a lesion. Once the guide wire shaft is in place, the guide wire can be removed, and a filter sheath containing a filter assembly disposed about the filter wire can be retracted to deploy an embolic filter within the vessel. Once occluded, the embolic filter can be again collapsed by sliding the filter sheath over the filter assembly, and then withdrawn from the vessel.

BRIEF DESCRIPTION OF THE DRAWINGS

FIG. 2 includes FIGS. 2A & 2B which illustrate different embodiments of a delivery and retrieval sheath of the present invention; wherein:

FIG. 3 includes FIGS. 3A-F which illustrate an embolic filter system of the present invention and a method for using same; wherein:

FIG. 4 includes FIGS. 4A-4D which illustrate a filter exchange system in accordance with an another embodiment of the present invention; wherein:

FIG. 4A illustrates a guide wire inserted into a vessel at a location distal to a stenotic region.

FIG. 4B illustrates a filter exchange system having a guide wire shaft, a guide wire lumen, a filter and a filter lumen advanced to a distal portion of the guide wire shown in FIG. 4A;

FIG. 4C illustrates the filter exchange system of FIG. 4B, wherein the guide wire has been withdrawn; and FIG. 4D illustrates the embolic filter in the filter exchange system of FIG. 4B in a fully deployed state at a location distal to the stenotic region.

FIG. 5 includes FIGS. 5A-5E which illustrate a filter exchange system in accordance with yet another embodiment of the present invention; wherein:

DETAILED DESCRIPTION OF PREFERRED EMBODIMENTS

Rapid Exchange Embolic Filter System
Embolic Filter Assembly

An embolic filter assembly of the present invention is comprised of an embolic filter operatively coupled to a guide wire. A number of embolic filters are known for providing distal protection against embolization in conjunction with a transluminal diagnostic or therapeutic procedure, such as angioplasty or embolectomy. These embolic filters are deployed distal to a vascular lesion, such as a stenosis, prior to undertaking the diagnostic or therapeutic procedure, and are designed to collect emboli liberated during the procedure to prevent them from entering the blood stream. Generally, embolic filters suitable for use with the present invention are characterized by having a blood permeable sac and a support hoop which forms an opening into the sac; however, other types of filters are also useable with the present invention.

Figure 1:
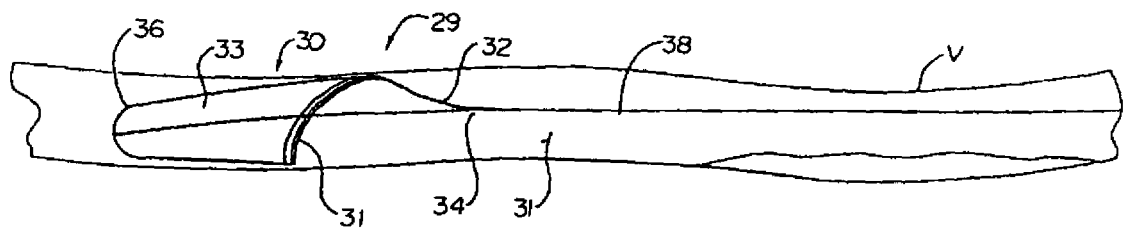
FIG. 1 illustrates an embolic filter suitable for use with the present invention.

Referring now to FIG. 1, a schematic of an embolic filter assembly suitable for use with the present invention is shown deployed within vessel V distal a lesion. Embolic filter assembly 29 includes embolic filter 30 and guide wire 38. Embolic filter 30 includes self-expanding support hoop 31, preferably mounted on suspension strut 32, which supports blood permeable sac 33. As such, support hoop 31 forms a mouth or proximal opening of sac 33 while blood permeable sac 33 provides a closed, but permeable distal end 36. Support hoop 31 is preferably formed of a super-elastic material, such as nitinol, and has a constrictable, preformed shape. Accordingly, support hoop 31 is collapsible to fit into a delivery and retrieval sheath, and then expandable to its preformed shape. Suspension strut 32 is attached to guide wire 38 at joint 34 by means of a solder bead or shrink tubing, for example.

Blood permeable sac 33 is preferably made of a material having a multiplicity of pores. Suitable materials include, but are not limited to, biocompatible polymeric materials such as polyethylene, polyproylene, polyurethane, polyester, polyethylene tetraphlalate, nylon, polytetrafluoroethylene, or combinations thereof. These pores, in turn, permit red blood cells to pass through the sac substantially unhindered, while capturing and retaining larger emboli and debris that may be released during an interventional procedure.

As described, blood permeable sac 33 is preferably comprised of a suspension strut 32 or other support means to hold support hoop 31 substantially concentric to guide wire 38, thereby allowing guide wire 38 to bend and move laterally without lifting support hoop 31 from the wall. Accordingly, suspension strut 32 advantageously permits support hoop 31 to become concentrically displaced relative to guide wire 38 when embolic filter 30 is deployed in a curved vessel.

Delivery and Retrieval Sheaths

As indicated above, an embolic filter assembly, e.g., embolic filter 30 operatively coupled to guide wire 38, is advanced to a target site within a vessel through a delivery and retrieval sheath. The delivery and retrieval sheath of the present invention, in turn, is used to advance, deliver, deploy and retrieve an embolic filter assembly to a target location within a vessel. In one embodiment of the present invention, the delivery and retrieval sheath includes two lumens for rapid delivery and retrieval of filter assemblies. In yet another embodiment of the present invention, the delivery and retrieval sheath includes three or more lumens for deployment and retrieval of additional filter assemblies, interventional therapeutic devices, diagnostic devices and/or stents. Each lumen has a proximal opening, and a distal opening.

Figure 2A:
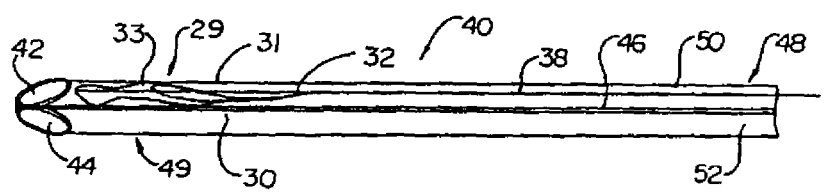
FIG. 2A illustrates one embodiment of a delivery and retrieval sheath of the present invention having at least two lumens and having an embolic filter system disposed therein.
Figure 2B:
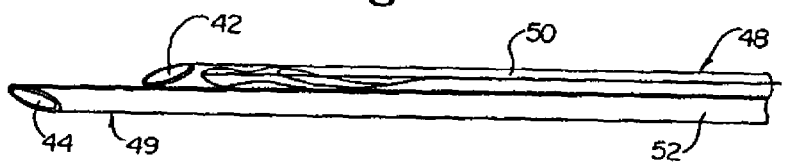
FIG. 2B illustrates another embodiment of a delivery and retrieval sheath of the present invention having lumens of differing lengths.

Referring to FIGS. 2A-B, various embodiments of delivery and retrieval sheaths suitable for use with the present invention will now be described. Delivery and retrieval sheath 40, shown in FIG. 2A includes a proximal end 48, a distal end 49 and two lumens 50 and 52 having distal openings 42 and 44 respectively. Lumens 50 and 52 share a common wall 46. In this particular embodiment, the distal ends of lumens 50 and 52 terminate at substantially the same point, i.e., the distal opening 42 of lumen 50 and distal opening 44 of lumen 52 are substantially even. Delivery and retrieval sheath 40 is shown with an embolic filter assembly therein, such as the embolic filter assembly 29 shown in FIG. 1. Accordingly, embolic filter 30 is in a folded or constricted or undeployed, pre-delivery state disposed within a first lumen 50 of delivery and retrieval sheath 40.

FIG. 2B shows an alternative embodiment of the delivery and retrieval sheath of FIG. 2A. In this particular embodiment, the distal end of lumen 50 terminates proximally of the distal end of lumen 52, such that distal opening 42 of lumen 50 is proximal of distal opening 44 of lumen 52. This particular embodiment advantageously minimizes the profile of sheath 40.

Methods

Methods of using the embolic filter system of the present invention will now be described in the context of an interventional therapeutic procedure, such as angioplasty, atherectomy, thrombectomy, stent placement or interventional diagnostic procedure, to treat and/or diagnose a lesion within a body lumen.

FIGS. 3A-3F illustrate the rapid exchange of embolic filters using an embodiment of the present invention. In practicing the subject invention, a generic guide wire (not shown) is manipulated into position in vessel V using well known percutaneous techniques. Once the generic guide wire is positioned, a multiple lumen delivery and retrieval sheath, such as the multiple lumen delivery and retrieval sheath 40 of FIG. 2A, may be tracked over the generic guide wire to guide the delivery and retrieval sheath within the vasculature, e.g., lumen 50 may be used to track over the generic guide wire. Once delivery and retrieval sheath 40 is maneuvered into a position within vessel V distal lesion 4, the generic guide wire may be removed from the vasculature. In certain embodiments, positioning of the delivery and retrieval sheath 40 may be based on the position of a radiopaque marker or the like under fluoroscopy.

Figure 3A:
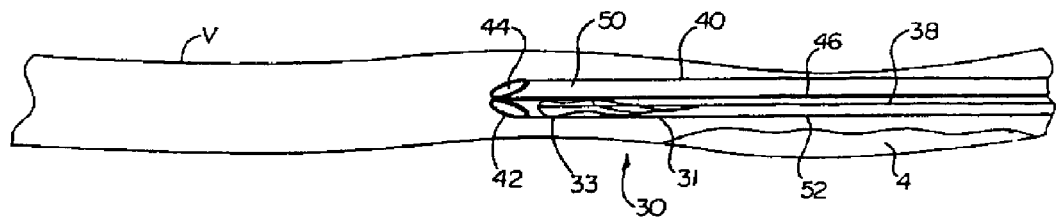
FIG. 3A illustrates the multiple lumen delivery and retrieval sheath of FIG. 2A with a first embolic filter of the present invention operatively coupled to a first guide wire and disposed in an undeployed, pre-delivery state within a first lumen of the sheath.

As shown in FIG. 3A, first embolic filter, such as embolic filter 30 of FIG. 1, is disposed within a lumen of delivery and retrieval sheath 40, for example first lumen 52 of delivery and retrieval sheath 40, and is operatively coupled to guide wire 38. FIG. 3A shows embolic filter 30 in its constricted, undeployed, pre-delivery state within lumen 52. Thus, delivery and retrieval sheath 40, with embolic filter 30 disposed therein, is advanced through the vessel over a generic guide wire to a site distal to lesion 4. Once delivery and retrieval sheath 40 is at the desired location distal lesion 4, the generic guide wire can be removed from the vasculature.

Figure 3B:
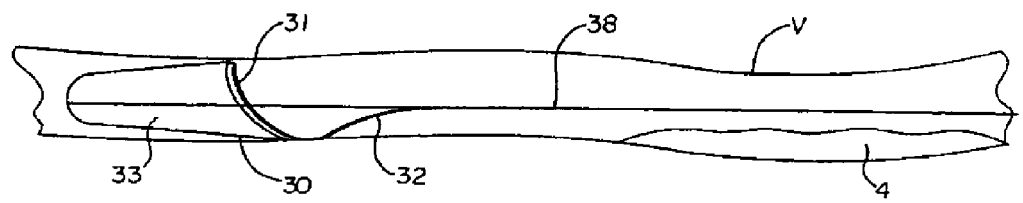
FIG. 3B illustrates the first embolic filter of FIG. 3A, now fully deployed inside a vessel at a location distal to a stenotic lesion.

Once the delivery and retrieval sheath 40 is appropriately positioned, guide wire 38 is held stationary while delivery and retrieval sheath 40 is retracted proximally to deploy embolic filter 30. Alternatively, delivery and retrieval sheath 40 may be held stationary while guide wire 38 is advanced distally. In either case, when embolic filter 30 is liberated from distal opening 42 of lumen 52 and is thus no longer confined to the delivery and retrieval sheath 40, support hoop 31 is expanded, as illustrated in FIG. 3B. Subsequent to filter deployment, delivery and retrieval sheath 40 is removed from the vasculature. FIG. 3B shows embolic filter 30 in its fully deployed state in vessel V, with support hoop 31 expanded to form an opening or mouth through which emboli and debris can flow into blood permeable sac 33.

After deployment of embolic filter 30 and subsequent removal of delivery and retrieval sheath 40, other interventional instruments, such as angioplasty catheters, atherectomy devices or stent delivery systems may be advanced along guide wire 38 to a position proximal of embolic filter 30. Thus, embolic filter 30 is positioned to trap emboli generated from the use of the interventional device on the lesion, e.g., pieces of plaque dislodged from the wall of vessel V by the interventional procedure.

Figure 3C:
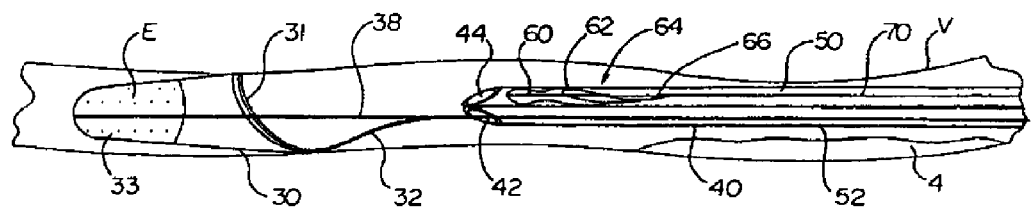
FIG. 3C illustrates the first embolic filter of FIG. 3B, substantially filled with emboli, and the multiple lumen delivery and retrieval sheath of FIG. 2A advanced to retrieve the deployed first filter and to deploy a second filter disposed within a second lumen of the multiple lumen delivery and retrieval sheath.
Figure 3D:
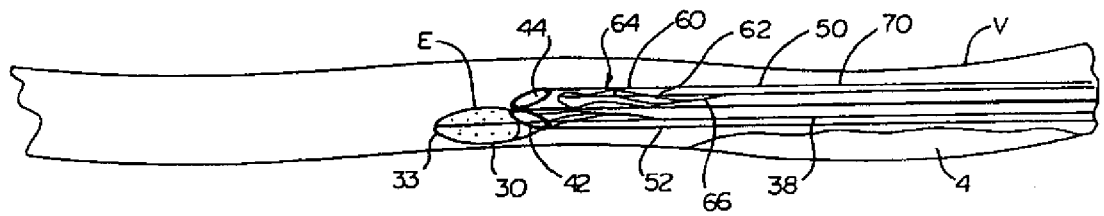
FIG. 3D illustrates the retrieval of the first embolic filter into the first lumen of the multiple lumen delivery and retrieval sheath.
Figure 3E:
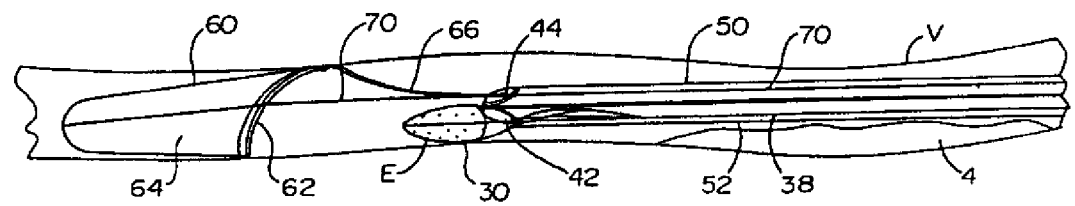
FIG. 3E illustrates the deployment of the second embolic filter into the vessel with the first embolic filter at least partially withdrawn into the first lumen of the multiple lumen delivery and retrieval sheath.

With respect to FIGS. 3C-3E, the exchange of first embolic filter 30 for a second embolic filter is shown. Accordingly, when first embolic filter 30 becomes full of emboli E, it is removed from the vasculature to prevent injury to the patient. If it is desirous to proceed with the interventional procedure, the first embolic filter may be exchanged for a second embolic filter. As such, the interventional device (not shown) is first removed from the vasculature by tracking it proximally over guide wire 38. Delivery and retrieval sheath 40 is again advanced over guide wire 38 to a site distal to lesion 4 and proximal to the now occluded first embolic filter 30. As illustrated in FIG. 3C, a second embolic filter assembly 64, including second embolic filter 60, support hoop 62 and suspension strut 66, is operatively coupled to guide wire 70 in second lumen 50 of delivery sheath 40 with second embolic filter 60 in a contracted or undeployed, pre-delivery state.

In FIG. 3D, once delivery and retrieval sheath 40 containing second embolic filter assembly 64 is advanced to the vicinity of first embolic filter 30, first embolic filter 30 is at least partially withdrawn proximally into first lumen 52 of delivery sheath 40. Alternatively, delivery sheath 40 can be advanced distally, at least partially over first embolic filter 30. In either case, the filter opening or mouth of first embolic filter 30 essentially closes or collapses such that emboli disposed in blood permeable sac 33 of first embolic filter 30 is effectively retained inside the sac 33.

Figure 3F:
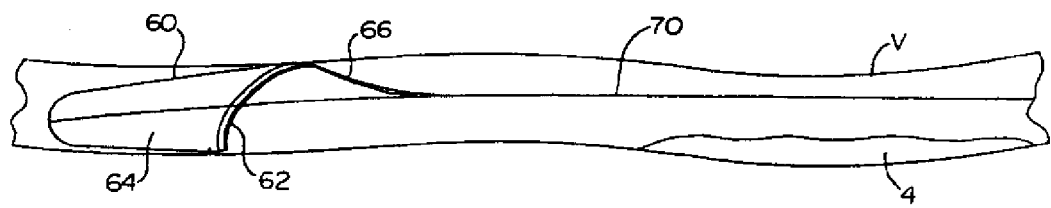
FIG. 3F illustrates the second embolic filter fully deployed within the vessel at a location distal to the stenotic region.

Referring now to FIG. 3E, once first embolic filter 30 is withdrawn at least partially into first lumen 52 to seal the contents therein, guide wire 70 is held stationary while delivery and retrieval sheath 40 with first embolic filter 30 are refracted proximally or, alternatively, delivery and retrieval sheath 40 with first embolic filter 30 may be held stationary while guide wire 70 is advanced distally. In either case, when second embolic filter 60 is liberated from distal opening 44 of second lumen 50 and is thus no longer confined to delivery and retrieval sheath 40, support hoop 62 is expanded. Once second embolic filter 60 is deployed in vessel V, delivery and retrieval sheath 40 along with first embolic filter 30 are removed from the vasculature. FIG. 3F shows second embolic filter 60 in its fully deployed state in vessel V, with support hoop 62 expanded to form an opening or mouth through which emboli and debris can flow into blood permeable sac 64. As such, an interventional device can be again guided to lesion 4 to continue the interventional procedure.

In certain embodiments, more than two embolic filters may be advanced, deployed and retrieved through multiple lumen delivery and retrieval sheath 40. As such, these additional embolic filters may be advanced, deployed and retrieved through additional lumens of a multiple lumen delivery and retrieval sheath. For example, a third embolic filter may be advanced, deployed and retrieved through a multiple lumen delivery and retrieval sheath defining three lumens. Alternatively, the additional filters may be advanced, deployed and retrieved through the same lumen as that which was used to advance, deploy and retrieve the first embolic filter. For example, a third embolic filter may be advanced, deployed and retrieved through first lumen 52 of multiple lumen delivery and retrieval sheaths 40 or 130 after the first embolic filter 30 has been withdrawn and removed therefrom. In either case, additional embolic filters may be advanced, deployed and removed as described above.

Exchange Sheaths

FIGS. 4A-4D illustrate a filter exchange system in accordance with a particular embodiment of the present invention. As shown in FIG. 4A, a guide wire 104 is inserted into vessel V and extends distally of a lesion 4. Guide wire 102 has a proximal end 170, a distal end 168, and a distal tip region 104.

As illustrated in FIG. 4B, a guide tip 150 defining a guide wire lumen 168 is advanced to a distal end 168 of guide wire 102. Guide tip 150 has a tapered profile, with a larger diameter portion on proximal end 152, and a smaller diameter portion on distal end 151. Guide tip 150 can be made from, for example, a relatively soft atraumatic polymer or a radiopaque coil. A filter sheath 154 defines a filter lumen 172 containing a filter assembly 174 therein. Disposed in part within filter lumen 172 is a filter wire 138 having a proximal end and a distal end 156. Distal end 156 of filter wire 138, in turn, is attached to the proximal end of guide tip 150 at flange 176. Filter wire 138 can be attached to guide tip 150 at flange 176 by, for example, molding tip 150 over flange 176. Alternatively, filter wire 138 can be attached to guide wire shaft 150 by means of a shrink-fit, adhesive, interference fit or other means.

In use, guide tip 150, operatively coupled to filter sheath 154 and filter assembly 174, can be advanced over guide wire 102 to a point within the vessel V distal lesion 4. As shown in FIG. 4B, embolic filter 133 is housed within filter lumen 172 in its un-deployed, collapsed state. Once filter assembly 174 is advanced distally of lesion 4 to a desired location within vessel V, guide wire 102 can be removed from guide tip 150, as illustrated in FIG. 4C. When filter assembly 174 is appropriately positioned, filter wire 138 is held stationary while filter sheath 154 is retracted proximally, allowing embolic filter 133 to deploy in the vessel. Alternatively, filter sheath 154 can be held stationary while filter wire 138 is advanced distally. In either case, when embolic filter 133 is removed from filter sheath 154 and thus no longer confined within filter lumen 172, embolic filter 133 can be fully deployed.

FIG. 4D illustrates filter assembly 158 in a deployed state after the removal of filter sheath 154. As shown in FIG. 4D, filter assembly 158 having an embolic filter 133, support hoop 136, suspension strut 162 and filter sac 180 is shown fully deployed at a point distal lesion 4. Suspension strut 162 is connected to support hoop 136 at its distal end, and to joint 140 at its proximal end. The proximal end of suspension strut 162 is attached to filter wire 138 by means of a solder bead or other attachment means. Alternatively, joint 140 can be a tube to allow rotation of guidewire 138. When the therapeutic procedure is completed, filter 133 can be retracted back into filter sheath 154 or other retrieval catheter and removed from the vessel. Alternatively, filter assembly 158 can be retracted back into filter sheath 154, or other retrieval catheter, by pulling filter guide wire 138 proximally until embolic filter 133 is encased in part with filter lumen 172. Although the filter assembly shown in FIGS. 4A-D is similar to the filter assembly discussed infra in FIG. 1, other embolic filters can be employed by the filter exchange system of FIGS. 4A-4D without departing from the scope of the subject invention.

Figure 5A:
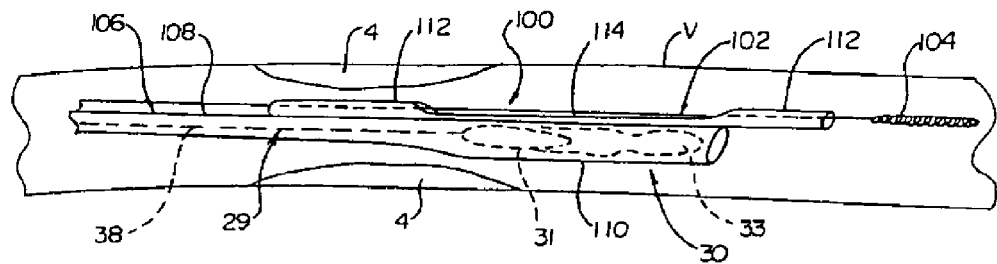
FIG. 5A illustrates an exchange sheath disposed over a guide wire and having a filter assembly disposed within the sheath.

FIG. 5A is an alternative embodiment of an exchange sheath in accordance with the present invention. As illustrated in FIG. 5A, filter assembly 30 is disposed along a filter guide wire 38 in an exchange sheath 100. Sheath 100 has a proximal end (not shown) and a distal end. Exchange sheath 100 further includes a filter sheath 106 defining a filter lumen. Filter sheath 106 includes a shaft 108 and a larger diameter portion 110 at the distal end of shaft 108. Larger diameter portion 110 at least in part contains filter 30 when filter guide wire 38 is disposed within the lumen of filter sheath 106.

Exchange sheath 100 also includes a guide wire sheath 112. As shown in FIG. 5A, guide wire sheath 112 can be substantially shorter than exchange sheath 100. Guide wire sheath 112 includes a guide wire lumen therethrough. In one advantageous embodiment, guide wire lumen 112 is discontinuous, and includes a skived portion 114 adjacent the larger diameter portion 110 of filter sheath 106. This can be done to reduce the profile of exchange sheath 100 at larger diameter portion 110. Moreover, a guide wire 102 having a distal spring tip 104 can be disposed within the guide wire lumen of sheath 112. Once the exchange sheath 100 containing collapsed and un-deployed embolic filter 30 is advanced along guide wire 102 to a portion of the vessel distal lesion 4, guide wire 102 can be removed from the vessel. Alternatively, embolic filter 30 can be first advanced along filter wire 38 distally until it is fully deployed within the vessel, at which point guide wire 102 can be removed from the vessel.

Figure 5B:
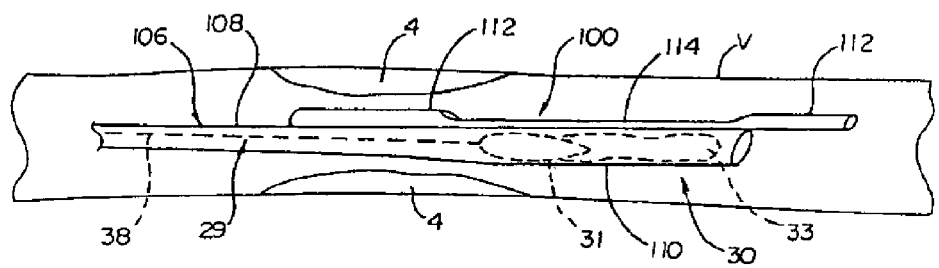
FIG. 5B illustrates the exchange sheath of FIG. 5A wherein the guide wire has been withdrawn.
Figure 5C:
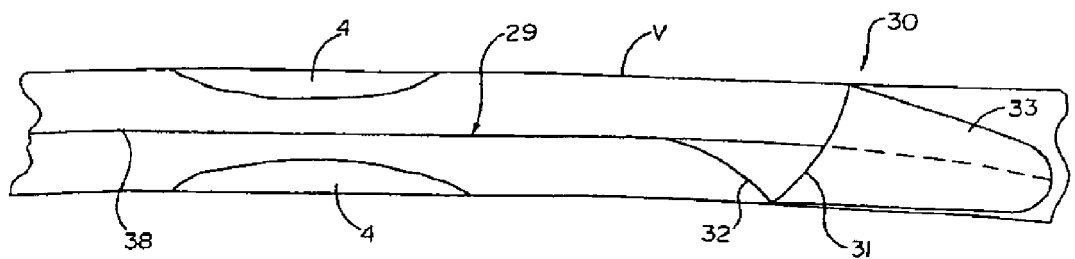
FIG. 5C illustrates the filter assembly of FIG. 5B wherein the exchange sheath has been withdrawn.

FIG. 5B illustrates the exchange sheath 100 in FIG. 5A subsequent to removal of the guide wire 102 from vessel V, but prior to deployment of embolic filter 30. As shown in FIG. 5B, once filter containing region 110 and filter 30 have been advanced distally of the lesion, and once guide wire 102 is withdrawn from the vessel, embolic filter 30 can be deployed within the vessel by either holding the filter wire 38 static and sliding shaft 108 proximally, or alternatively, by holding shaft 108 static and sliding the filter wire 38 distally. Once filter assembly 29 is disposed in vessel V, as shown in FIG. 5C, various devices such as angioplasty catheters or atherectomy catheters can be advanced over filter wire 38 to lesion 4.

Figure 5D:
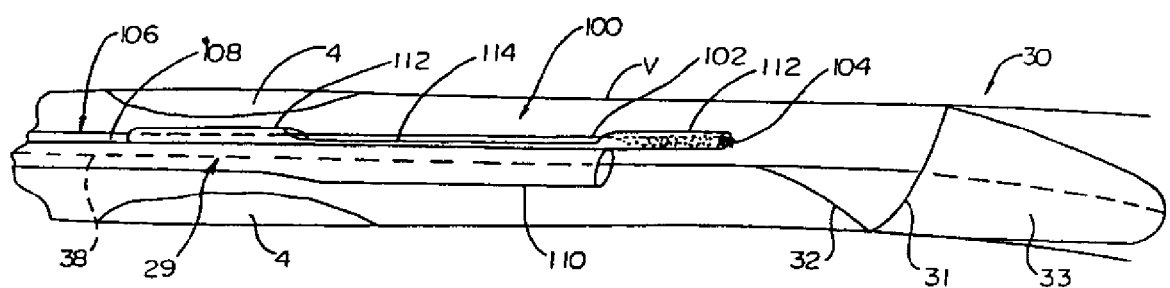
FIG. 5D illustrates the advancement of an exchange sheath and guide wire over the filter assembly of FIG. 5C.
Figure 5E:
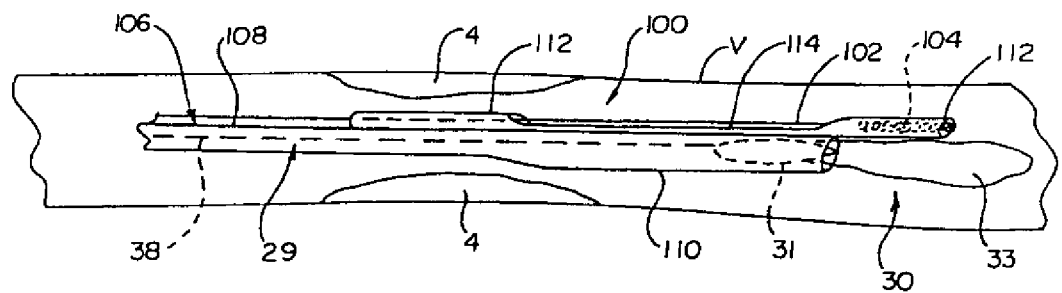
FIG. 5E illustrates the exchange sheath of FIG. 5D advanced over the filter assembly of FIG. 5C.

During angioplasty, atherectomy or other procedures, emboli can break free from lesion 4 and drift into filter sac 33. Emboli might eventually substantially fill filter sac 33, in whole or in part occluding vessel V. Embolic filter 30 can then be removed from vessel V by first removing the angioplasty catheter, atherectomy catheter or other device. Then, as shown in FIG. 5D, exchange sheath 100 and guide wire 102 can be advanced over filter wire 38. Filter 30 can then at least in part be collapsed and withdrawn from vessel V by drawing said filter into filter sheath 106, or advancing exchange sheath 100 including filter sheath 106 at least in part over embolic filter 30. Once filter 30 is at least in part in exchange sheath 100, filter assembly 29 and exchange sheath 100 can be removed proximally from vessel V over guide wire 102. Guide wire 102 is then left in place across the lesion. Another filter assembly 29 can then be placed in vessel V by repeating the steps described above beginning with FIG. 5A.

Kits

Also provided by the subject invention are kits for use in practicing the subject methods. A kit of the subject invention includes at least one embolic filter assembly and at least one multiple lumen delivery and retrieval sheath, as described above. Other kits may include one or more embolic filter assemblies without the accompanying multiple lumen delivery and retrieval sheath. Certain kits may include one or more vascular interventional systems, such as an angioplasty system, a stent placement system, an atherectomy system, an embolectomy system and a diagnostic system in addition to a subject embolic filter assembly and/or multiple lumen delivery and retrieval sheath. Finally, the subject kits preferably include instructions for using the subject device(s) and system(s) during an interventional procedure to protect the patient against emboli. These instructions may be present in one or more of the instructions for use included in the kits, packaging, label inserts or containers present in the kits, and the like.

It is evident from the above description that the subject inventions provide a significant contribution to the field of embolic protection. It is recognized that departures from the described embodiments may be made which are within the scope of the invention, and that obvious modifications will occur to one skilled in the art upon reading this disclosure. Such departures and modifications that come within the meaning and range of equivalents of the disclosed concepts are intended to be included within the scope of the appended claims.

What is claimed:

1. A system for delivering and retrieving multiple embolic filters which employs a single delivery and retrieval sheath, the system comprising:

a first filter wire segment having a distal region and a proximal region;

a first embolic filter deployable from the first filter wire segment and operatively coupled to the distal region thereof;

a second filter wire segment having a distal region and a proximal region;

a second embolic filter deployable from the second filter wire segment and operatively coupled to the distal region thereof;

a delivery and retrieval sheath having a distal end, a proximal end, and at least one lumen therebetween configured and adapted to slidably contain a filter wire;

a first distal sheath segment associated with the distal end of the delivery and retrieval sheath, said first distal sheath segment having a lumen configured and adapted to contain the first embolic filter in a collapsed state; and a second distal sheath segment associated with the distal end of the delivery and retrieval sheath, said second distal sheath segment having a lumen configured and adapted to contain the second embolic filter in a collapsed state, wherein the first filter wire segment passes at least in part through the lumen of the first distal sheath segment, further wherein the second filter wire segment passes at least in part through the lumen of the second distal sheath segment, and wherein the first and second distal sheath segments are configured and adapted to deploy the respective first and second filters at locations which are longitudinally displaced from each other.

2. The system of claim 1, further comprising a rapid exchange guidewire lumen.

3. The system of claim 1, wherein the first and second embolic filters may be deployed sequentially.

4. The system of claim 1, wherein the first and second embolic filters may be deployed simultaneously.

5. The system of claim 1, wherein the first and second embolic filters may be retrieved sequentially.

6. The system of claim 1, wherein the first and second embolic filters may be retrieved simultaneously.

7. A method of delivering and retrieving multiple embolic filters which employs a single delivery and retrieval sheath, the method comprising:

advancing a delivery and retrieval sheath having a distal end, a proximal end, and at least one lumen therebetween configured and adapted to slidably contain a filter wire, a first distal sheath segment having a lumen configured and adapted to contain a first embolic filter in a collapsed state, a second distal sheath segment having a lumen configured and adapted to contain a second embolic filter in a collapsed state to a point in a vessel downstream of a potential source of embolic debris, said first and second embolic filters being contained within their respective sheaths and operatively coupled to the respective distal regions of the first and second filter wire segments;

moving the first embolic filter relative to the first distal sheath segment, thereby deploying the first embolic filter from the first filter wire segment;

moving the second embolic filter relative to the second distal sheath segment, thereby deploying the second embolic filter from the second filter wire segment;

passing blood through at least one of the first and second embolic filters;

moving the first embolic filter relative to the first distal sheath segment, thereby receiving the first embolic filter within the first distal sheath segment in a collapsed state;

moving the second embolic filter relative to the second distal sheath segment, thereby receiving the second embolic filter within the second distal sheath segment in a collapsed state; and removing the delivery and retrieval sheath and first and second embolic filters from the vessel.

8. The method of claim 7, wherein the first and second embolic filters may be deployed sequentially.

9. The method of claim 7, wherein the first and second embolic filters may be deployed simultaneously.

10. The method of claim 7, wherein the first and second embolic filters may be retrieved sequentially.

11. The method of claim 7, wherein the first and second embolic filters may be retrieved simultaneously.

* * * * *